US012721792B2

(12) United States Patent
Kashiki et al.

(10) Patent No.: US 12,721,792 B2
(45) Date of Patent: Sep. 1, 2026

(54) PASTE-LIKE DENTAL GLASS COMPOSITION

(71) Applicant: Kuraray Noritake Dental Inc., Kurashiki (JP)

(72) Inventors: Nobusuke Kashiki, Aichi (JP); Yuta Takeuchi, Aichi (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 582 days.

(21) Appl. No.: 18/039,782

(22) PCT Filed: Dec. 1, 2021

(86) PCT No.: PCT/JP2021/044173
§ 371 (c)(1),
(2) Date: Jun. 1, 2023

(87) PCT Pub. No.: WO2022/118905
PCT Pub. Date: Jun. 9, 2022

(65) Prior Publication Data

US 2024/0033187 A1 Feb. 1, 2024

(30) Foreign Application Priority Data

Dec. 2, 2020 (JP) ................................. 2020-200643

(51) Int. Cl.

| | |
|---|---|
| ***A61K 6/836*** | (2020.01) |
| ***A61C 5/70*** | (2017.01) |
| ***A61C 9/00*** | (2006.01) |
| ***A61C 13/083*** | (2006.01) |
| ***A61C 19/04*** | (2006.01) |
| ***A61C 19/045*** | (2006.01) |
| ***A61C 19/05*** | (2006.01) |
| ***A61K 6/15*** | (2020.01) |
| ***A61K 6/77*** | (2020.01) |
| ***C03C 3/093*** | (2006.01) |
| ***C03C 4/00*** | (2006.01) |
| ***C03C 8/04*** | (2006.01) |
| ***C03C 8/16*** | (2006.01) |
| ***C03C 10/00*** | (2006.01) |

(52) U.S. Cl.
CPC ................ *A61K 6/836* (2020.01); *A61C 5/70* (2017.02); *A61C 9/004* (2013.01); *A61C 9/0053* (2013.01); *A61C 13/083* (2013.01); *A61C 19/04* (2013.01); *A61C 19/045* (2013.01); *A61C 19/05* (2013.01); *A61K 6/15* (2020.01); *A61K 6/77* (2020.01); *C03C 3/093* (2013.01); *C03C 4/0021* (2013.01); *C03C 8/04* (2013.01); *C03C 8/16* (2013.01); *C03C 10/0018* (2013.01)

(58) Field of Classification Search
CPC . A61K 6/836; A61K 6/15; A61K 6/77; A61C 5/70; A61C 9/004; A61C 9/0053; A61C 19/04; A61C 19/045; A61C 19/05; A61C 13/083; C03C 8/04; C03C 8/16; C03C 10/0018; C03C 3/093; C03C 4/0021
See application file for complete search history.

(56) References Cited

U.S. PATENT DOCUMENTS

| | | | |
|---|---|---|---|
| 6,444,597 | B1 | 9/2002 | Sato et al. |
| 2015/0342838 | A1 | 12/2015 | Hara et al. |
| 2020/0330331 | A1 | 10/2020 | Kawata et al. |

FOREIGN PATENT DOCUMENTS

| | | | |
|---|---|---|---|
| JP | H03-77804 | A | 4/1991 |
| JP | H05-139926 | A | 6/1993 |
| JP | 2001079019 | A | 3/2001 |
| JP | 2009143839 | A | 7/2009 |
| JP | 2015227312 | A | 12/2015 |
| JP | 2017193492 | A | 10/2017 |
| JP | 2020117499 | A | 8/2020 |

OTHER PUBLICATIONS

Machine English translation of JP 1991-077804, Kurahashi et al., Apr. 3, 1991.*
International Search Report issued Jan. 25, 2022 in PCT/JP2021/044173 (with English translation), 4 pages.
Written Opinion issued Jan. 25, 2022 in PCT/JP2021/044173 (with English translation), 10 pages.
Extended European Search Report issued Feb. 5, 2025, received Feb. 22, 2025, in corresponding European Patent Application No. 21900656.6, 8 pages.

* cited by examiner

*Primary Examiner* — Patrick D Niland
(74) *Attorney, Agent, or Firm* — Element IP, PLC

(57) ABSTRACT

The present invention provides a paste-like dental glass composition having good ease of handling due to a reduction in paste runniness while enabling accurate shade adjustments with no discoloration to hues such as black or grey after firing. The present invention relates to a paste-like dental glass composition comprising a glass powder (A), and an organic solvent (B) having two or less hydroxyl groups within the molecule and a viscosity at 20° C. of 2,500 mPa·s or less, and being essentially free of an organic compound having three or more hydroxyl groups within the molecule.

13 Claims, No Drawings

PASTE-LIKE DENTAL GLASS COMPOSITION

TECHNICAL FIELD

The present invention relates to a paste-like dental glass composition used for prosthetic restorations such as artificial teeth similar in aesthetics to natural teeth, and that, while being easy to handle for dental technicians performing a manual build-up, does not change its color to hues such as black or grey after firing.

BACKGROUND ART

Ceramics have a transparent look and shades similar to natural teeth, and are indispensable for the fabrication of crowns, which requires attention to aesthetics.

In a typical process of crown fabrication, a dental liquid mixture containing components such as porcelain, water, and an organic solvent, or a paste-like porcelain prepared by mixing ceramic with components such as water and an organic solvent is used to fabricate a crown by a repeated procedure involving building up such a material on a frame covering an abutment tooth (for example, a metal frame, a ceramic frame), and firing the material. The use of dental porcelain is expected to increase, particularly in response to the continuously growing demand for ceramic materials and the associated increase in individual demand for better aesthetics.

Such a paste-like porcelain uses a low-volatile solvent so as to prevent the porcelain from drying as a result of evaporation of components such as water or an organic solvent while the procedure is being performed by a dental technician. Because porcelain typically contains a fine glass powder, the solvent is required to be highly compatible with the powder so that the paste properties can be adjusted to provide good ease of handling in the procedure performed by a dental technician. Another requirement is that no organic materials remain after firing, because any remaining organic material can cause discoloration after firing (mostly, grey to black discoloration).

For example, Patent Literature 1 discloses a paste-like dental porcelain comprising a component in which a polymeric material having a synthetic and/or natural hydrophilic group is dissolved in water and/or one organic solvent or two or more organic solvents selected from a dihydric or trihydric alcohol, an ether with a remaining hydroxyl group, and hydroxy(meth)acrylate. It is proposed that the polymeric material efficiently undergoes decomposition and combustion after porcelain build-up.

Patent Literature 2 discloses a paste-like dental porcelain comprising a colorant that decolors during firing, an organic solvent, and a porcelain powder. It is proposed that no organic materials remain after firing, and no discoloration takes place.

However, it was found that, in Patent Literatures 1 and 2, the organic materials remain after firing depending on the temperature of the firing after porcelain build-up, black or grey discoloration occurs. It was also found that, depending on the choice of organic solvent (for example, glycerin; boiling point: 290° C.) or polymeric material (for example, methyl cellulose), a condensation reaction or polymerization reaction with the boron component contained in the porcelain powder occurs during firing after porcelain build-up, and firing leaves organic materials, and causes discoloration to hues such as black or grey.

CITATION LIST

Patent Literature

Patent Literature 1: JP 2001-079019 A
Patent Literature 2: JP 2017-193492 A

SUMMARY OF INVENTION

Technical Problem

It is accordingly an object of the present invention to provide a paste-like dental glass composition having good ease of handling due to a reduction in paste runniness while enabling accurate shade adjustments with no discoloration to hues such as black or grey after firing.

Solution to Problem

The present inventors conducted intensive studies to find a solution to the foregoing problems, and found that the above issues can be solved with a paste-like dental glass composition comprising a glass powder (A), and a specific organic solvent (B) having two or less hydroxyl groups within the molecule. The invention was completed after further studies.

Specifically, the present invention includes the following.

[1] A paste-like dental glass composition comprising a glass powder (A), and an organic solvent (B) having two or less hydroxyl groups within the molecule and a viscosity at 20° C. of 2,500 mPa·s or less, and being essentially free of an organic compound having three or more hydroxyl groups within the molecule.

[2] The paste-like dental glass composition according to [1], which further comprises a thickener (C), the thickener (C) comprising at least one selected from the group consisting of an organic compound (C-1) having a viscosity at 20° C. of more than 2,500 mPa·s, an organic compound (C-2) that is solid at ordinary temperature, and an inorganic compound (C-3).

[3] The paste-like dental glass composition according to [1] or [2], wherein the organic solvent (B) is a dihydric alcohol compound.

[4] The paste-like dental glass composition according to any one of [1] to [3], wherein the organic solvent (B) is a dihydric alcohol compound having a C3 to C20 branched chain.

[5] The paste-like dental glass composition according to [4], wherein the dihydric alcohol compound having a C3 to C20 branched chain comprises at least one selected from the group consisting of 2-methyl-1,3-propanediol, 2-methyl-1,4-butanediol, 3-methyl-1,3-butanediol, 2-methyl-2,4-pentanediol, 3-methyl-1,5-pentanediol, 2,4-diethyl-1,5-pentanediol, and 2-ethyl-1,3-hexanediol.

[6] The paste-like dental glass composition according to any one of [1] to [5], wherein the organic solvent (B) has a boiling point of 100 to 350° C.

[7] The paste-like dental glass composition according to any one of [1] to [6], wherein the organic solvent (B) has a viscosity at 20° C. of 20 mPa·s or more.

[8] The paste-like dental glass composition according to any one of [1] to [7], wherein the glass powder (A) has a glass transition temperature of 400 to 600° C.

[9] The paste-like dental glass composition according to any one of [1] to [8], wherein the glass powder (A) has a softening point of 500 to 680° C.

[10] A method for producing a dental prosthesis, comprising the step of firing a paste-like dental glass composition of any one of [1] to [9] at 700 to 1,050° C.

[11] A method for producing a paste-like dental glass composition of any one of [1] to [9], which comprises the step of mixing a glass powder (A), and an organic solvent (B) having two or less hydroxyl groups within the molecule and a viscosity at 20° C. of 2,500 mPa·s or less.

Advantageous Effects of Invention

A paste-like dental glass composition of the present invention has good ease of handling due to a reduction in paste runniness while enabling accurate shade adjustments with no organic materials remaining after firing to cause discoloration. This makes it easier to adjust the shade of porcelain. A paste-like dental glass composition of the present invention excels in ease of handling because the paste does not dry during build-up.

DESCRIPTION OF EMBODIMENTS

Preferred embodiments of the present invention are described below.

A paste-like dental glass composition of the present invention comprises a glass powder (A), and an organic solvent (B) having two or less hydroxyl groups within the molecule and a viscosity at 20° C. of 2,500 mPa·s or less (hereinafter, also referred to simply as "organic solvent (B)"), and is essentially free of an organic compound having three or more hydroxyl groups within the molecule.

A paste-like dental glass composition of the present invention has good aesthetics after firing, and assumes a burn-off state after firing. Here, the definition of "burn-off" includes (1) no darkening of the shade by residual organic material after firing, and (2) the absence of large bubbles after firing.

<Glass Powder (A)>

The glass powder (A) contained in a paste-like dental glass composition of the present invention is described first.

The glass powder (A) used for a paste-like dental glass composition of the present invention is not particularly limited, as long as it is usable for dental glass compositions. The glass powder (A) may comprise a crystal. Examples of a glass powder material include a glass or crystallized glass containing $SiO_2$ as a main component (the material with the highest content, for example, 45 mass % or more, 50 mass % or more, or 55 mass % or more). Aside from $SiO_2$, such glasses may contain components such as $Al_2O_3$, $B_2O_3$, ZnO, $K_2O$, $Na_2O$, $Li_2O$, $ZrO_2$, CaO, MgO, or $Sb_2O_3$. The content of $SiO_2$ in the glass may be, for example, 55 to 75 mass %, 57 to 72 mass %, or 58 to 70 mass %. The content of $Al_2O_3$ may be 3 to 18 mass %, 3.5 to 16 mass %, or 4 to 15 mass %. The content of $B_2O_3$ may be 0 to 25 mass %, 0 to 20 mass %, or 0 to 18 mass %. The content of ZnO may be 0 to 5 mass %, 0 to 3 mass %, or 0 to 1 mass %. The content of $K_2O$ may be 0 to 10 mass %, 0 to 9 mass %, or 0 to 8 mass %. The content of $Na_2O$ may be 0 to 10 mass %, 1 to 9 mass %, or 1 to 8 mass %. The content of $Li_2O$ may be 0 to 1.5 mass %, 0 to 1.0 mass %, or 0 to 0.9 mass %. The content of CaO may be 0 to 10 mass %, 0 to 9 mass %, or 0 to 8 mass %. The content of $ZrO_2$ may be 0 to 5 mass %, 0 to 4 mass %, or 0 to 3 mass %. The content of MgO may be 0 to 10 mass %, 0 to 9 mass %, or 0 to 8 mass %. The content of $Sb_2O_3$ may be 0 to 3 mass %, 0 to 2 mass %, or 0 to 1 mass %. Specifically, at least one of amorphous-type potassium aluminosilicate glass ($4SiO_2 \cdot Al_2O_3 \cdot K_2O$), leucite crystal-type potassium aluminosilicate glass, fluoroapatite glass, and lithium silicate glass may be used. Particularly preferred is leucite crystal-type potassium aluminosilicate glass. Examples of the crystal include leucite, potassium feldspar, fluorophlogopite, diopside, mica, β-spodumene ($LiAlSi_2O_6$), β-calcium metaphosphate, apatite, magnesium titanate, β-eucryptite, and alumina. The glass powder (A) may be used alone, or two or more thereof may be used in an appropriate combination, depending on applications such as porcelain-fused-to-metal, all ceramics, and laminate veneers.

A wide range of commonly used ceramic raw materials can be used as raw material substances of glass powder (A). For example, it is possible to use components such as $SiO_2$, $Al_2O_3$, $B_2O_3$, ZnO, $K_2O$, $Na_2O$, $Li_2O$, $ZrO_2$, CaO, MgO, $Sb_2O_3$, $CeO_2$, BaO, or $SnO_2$ itself, and/or substances that can turn into such components by being heated in the atmosphere. In this case, the type of raw material to prepare is decided, and these are mixed after determining the composition of glass by calculation. The method of mixing raw material substances is not particularly limited. The preferred method is to uniformly disperse the raw material substances.

The mixed raw material substances are subjected to a heat treatment at about 700° C. or more to generate glass. The method of heat treatment is not particularly limited, as long as all the mixed raw material substances dissolve and uniformly become amorphous, without undergoing changes such as sublimation of components. The method used to subsequently cool the melt is not limited either, and the melt may be cooled by a method such as air cooling.

The clump of glass obtained in this fashion is pulverized, and classified into a powder having an adjusted particle size. The method used for the pulverization of a glass clump, and the method of classification are not particularly limited. It is possible to use a pulverizer, for example, such as a compression mill (e.g., a jaw crusher, and a cone crusher), a ball mill (e.g., a vibration ball mill, and a planetary mill), a stirred media mill (e.g., a tower mill, a stirred bed mill, and an annular mill), a high-speed rotary impact mill (e.g., a pin mill, and a disc mill), a roll mill, a jet mill, or an autogenous mill. Examples of classification devices include classifiers (such as a vibration sieve and a sifter), centrifugal classifiers (such as a cyclone), and wet classifiers (such as a sedimentation classifier). Preferably, the pulverizers and classification devices are ones coated with a material such as resin or glass, in order to prevent inclusion of metal impurities.

In the present invention, the components and their contents in the glass powder (A) are not particularly limited. It is, however, preferable to contain a boron component because it can lower the glass transition temperature or softening point to enable firing at lower temperatures, and reduce the firing time, for example. In the present invention, the condensation reaction or polymerization reaction with the boron component can be reduced, and, accordingly, the organic materials do not remain, and there is no discoloration to hues such as black or grey after firing, even when the glass powder (A) has a high boron component content. For example, the organic materials do not remain, and there will be no discoloration to hues such as black or grey after firing even when the content of the boron component is 2.0 mass % or more, 5.0 mass % or more, 10 mass % or more, or 15 mass % or more with respect to the whole of glass powder (A).

In view of considerations such as the ability to enable firing at lower temperatures and reduce the firing time, the glass powder (A) has a glass transition temperature of preferably 400 to 600° C., more preferably 420 to 580° C., even more preferably 450 to 550° C. In the same respect, the glass powder (A) has a softening point of preferably 500 to 680° C., more preferably 520 to 650° C., even more preferably 550 to 630° C. Running may occur during firing when the glass transition temperature is less than 400° C., or when the softening point is less than 500° C. When the glass transition temperature is higher than 600° C., or when the softening point is higher than 680° C., firing cannot be carried out at low temperature, and high firing temperatures are needed. This may cause deformation in a ceramic frame fabricated with a material such as lithium disilicate glass ceramics. The measurement methods of glass transition temperature and softening point are as described in the EXAMPLES section below.

The coefficient of linear thermal expansion (50 to 500° C.) of glass powder (A) can be appropriately selected according to factors such as the material of abutment teeth, or the frame material, and is not particularly limited. The glass powder (A) may have a coefficient of linear thermal expansion (50 to 500° C.) of about $4.0\times10^{-6}$ to $6.0\times10^{-6}$/° C. In another certain embodiment, the glass powder (A) may have a coefficient of linear thermal expansion (50 to 500° C.) of about $6.1\times10^{-6}$ to $13.5\times10^{-6}$/° C., or about $6.3\times10^{-6}$ to $12.5\times10^{-6}$/° C. For example, the glass powder (A) is preferably one having a coefficient of linear thermal expansion (50 to 500° C.) of about $9.0\times10^{-6}$ to $11.0\times10^{-6}$/° C. when the paste-like dental glass composition is used as a dental porcelain for frames containing zirconia as a main component (for example, 50 mass % or more, or 70 mass % or more). The glass powder (A) is preferably one having a coefficient of linear thermal expansion (50 to 500° C.) of about $6.1\times10^{-6}$ to $8.8\times10^{-6}$/° C. when the paste-like dental glass composition is used as a dental porcelain for frames containing alumina as a main component (for example, 50 mass % or more, or 70 mass % or more). The coefficient of linear thermal expansion can be measured by heating a specimen from room temperature to 500° C. with a thermomechanical analyzer TMA8311 (manufactured by Rigaku Corporation; a rate of temperature increase: 5° C./min). The coefficient of linear thermal expansion can be adjusted using a known method, for example, by adjusting the $K_2O$ content.

The glass powder (A) may comprise pigments such as inorganic pigments or opacifiers. Examples of inorganic pigments that may be contained in the glass powder (A) include praseodymium oxide, vanadium oxide, iron oxide, nickel oxide, chromium oxide, manganese oxide, cerium oxide, tin oxide compounds (for example, tin(II) oxide, tin(IV) oxide, or a compound oxide with a tin(IV) oxide component (for example, such as vanadium tin yellow, or chromium tin pink)), bismuth vanadium yellow, vanadium zirconium yellow, praseodymium yellow, cobalt blue, manganese pink, chromium alumina pink, zinc iron chromate, titanium oxide ($TiO_2$), and zirconium oxide ($ZrO_2$). Examples of the opacifiers include zirconium silicate, tin (IV) oxide, zirconium oxide ($ZrO_2$), zinc oxide, titanium oxide ($TiO_2$), and aluminum oxide. These are contained as appropriate according to the desired shade. The pigment may be used alone, or two or more thereof may be used in combination.

The glass powder (A) may be one that is surface treated with a surface treatment agent. The surface treatment agent may be, for example, a silane coupling agent. The silane coupling agent is not particularly limited. Examples include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(2-methoxyethoxy)silane, 3,3,3-trifluoropropyltrimethoxysilane, methyl-3,3,3-trifluoropropyldimethoxysilane, 2-(3,4-epoxycyclohexyl)ethyltrimethoxysilane, 3-glycidoxypropyltrimethoxysilane, 3-glycidoxypropylmethyldiethoxysilane, 3-glycidoxypropyltriethoxysilane, 3-methacryloxypropylmethyldimethoxysilane, γ-methacryloxypropylmethyldiethoxysilane, N-β(aminoethyl)γ-aminopropylmethyldimethoxysilane, N-β(aminoethyl)γ-aminopropyltrimethoxysilane, N-β(aminoethyl)γ-aminopropyltriethoxysilane, 3-aminopropyltrimethoxysilane, 3-aminopropyltriethoxysilane, N-phenyl-γ-aminopropyltrimethoxysilane, 3-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloxyalkyltrimethoxysilane (3 to 12 carbon atoms between the (meth)acryloxy group and the silicon atom; e.g., γ-methacryloxypropyltrimethoxysilane), and ω-(meth)acryloxyalkyltriethoxysilane (3 to 12 carbon atoms between the (meth) acryloxy group and the silicon atom; e.g., γ-methacryloxypropyltriethoxysilane). The surface treatment agent may be used alone, or two or more thereof may be used in combination.

The glass powder (A) may be a commercially available product. The commercially available product may be one containing an inorganic pigment. When a commercially available product containing no inorganic pigment is used as glass powder (A), the commercially available product may be used after adding an inorganic pigment. Examples of commercially available products that can be used as a glass powder (A) containing an inorganic pigment include Cerabien® ZR (manufactured by Kuraray Noritake Dental Inc. under this trade name), and Cerabien® ZR Press (manufactured by Kuraray Noritake Dental Inc. under this trade name). Examples of other commercially available products include Vintage AL and Vintage ZR (manufactured by Shofu Inc. under these trade names), NobelRondo (manufactured by Nobel Biocare Japan Co., Ltd. under this trade name), and Cercon Ceram S (manufactured by DENTSPLY-Sankin K.K. under this trade name).

The content of glass powder (A) is not particularly limited, and is preferably 50 to 90 mass %, more preferably 52 to 88 mass %, even more preferably 54 to 84 mass % with respect to the whole of a paste-like dental glass composition of the present invention. When the content of glass powder (A) is more than 90 mass %, it may be difficult to form a paste because of reduced kneadability between glass powder (A) and organic solvent (B). When the content of the glass powder is less than 50 mass %, poor ease of handling may result during a build-up because of a viscosity decrease in the kneaded product of glass powder and organic solvent. In the present specification, the upper limits and lower limits of numeric ranges (for example, ranges of contents of components, ranges of values calculated from components, and ranges of physical properties) are not particularly limited, and can be appropriately combined, as long as it does not hinder the effects of the present invention.

The particle diameter of glass powder (A) can be set according to the location of use, and is not particularly limited. The glass powder (A) has a particle diameter of preferably 1.0 to 10 μm. For example, in applications as opaque porcelain, the average particle diameter of the powder in the glass powder (A) contained in the paste-like dental glass composition is preferably 3.0 to 10 μm. The average particle diameter is preferably 1.0 to 7.0 μm in the case of powder porcelain used for staining.

The average particle diameter of glass powder (A) can be determined by a measurement using a laser diffraction scattering method. Specifically, a laser diffraction scattering method can be used to measure average particle diameter by volume, using, for example, a laser diffraction particle size distribution analyzer (SALD-2300 manufactured by Shimadzu Corporation) with a 0.2% sodium hexametaphosphate aqueous solution used as a dispersion medium.

<Organic Solvent (B)>

The following describes the organic solvent (B).

It is required that the organic solvent (B) be an organic solvent having two or less hydroxyl groups within the molecule, in order to reduce the condensation reaction or polymerization reaction with the boron component contained in the glass powder. When an organic solvent is used that has three or more hydroxyl groups within the molecule, a condensation reaction or polymerization reaction proceeds with the boron component contained in the glass powder during firing after build-up. This impairs the burn-off process, leaving residual organic materials after firing, and causing discoloration to hues such as black or grey. The organic solvent (B) is therefore essentially free of an organic solvent having three or more hydroxyl groups within the molecule. The content of an organic solvent having three or more hydroxyl groups within the molecule may be, for example, 1,000 ppm or less by mass, preferably 100 ppm or less by mass, more preferably 10 ppm or less by mass, even more preferably 1 ppm or less by mass, particularly preferably 0.1 ppm or less by mass, most preferably 0 ppm by mass relative to the mass of the paste-like dental glass composition. Examples of organic solvents having three or more hydroxyl groups within the molecule include trihydric alcohol compounds such as glycerin, 1,2,4-butanetriol, 1,2,3-butanetriol, and 1,2,6-hexanetriol.

When an organic solvent having an excessively high viscosity is solely used as organic solvent (B), difficulty may arise in preparing a paste due to the excessive viscosity. In this regard, the viscosity at 20° C. is 2,500 mPa·s or less. In view of kneadability and paste viscosity, the viscosity at 20° C. is preferably 2,100 mPa·s or less, more preferably 1,700 mPa·s or less, even more preferably 1,300 mPa·s or less. In order to adjust the paste properties to provide good ease of handling that does not involve runniness, it is preferable to use an organic solvent having a viscosity at 20° C. of 20 mPa·s or more, more preferably 50 mPa·s or more, even more preferably 100 mPa·s or more, particularly preferably 150 mPa·s or more.

In order to meet the need for the burn-off process to more sufficiently take place but to such an extent that it does not affect the shade after firing, the organic solvent (B) of the present invention is preferably one having a boiling point of 350° C. or less, more preferably 320° C. or less, even more preferably 300° C. or less, particularly preferably 280° C. or less. When an organic solvent is used that has a boiling point of less than 100° C., the organic solvent volatilizes even under room temperature, and drying of the paste proceeds. Because this may pose a difficulty in stably maintaining the paste properties and achieving the ease of handling needed for build-up, it is preferable to use an organic solvent having a boiling point of 100° C. or more. The organic solvent (B) is preferably one having a boiling point of 100 to 350° C., more preferably 100 to 320° C., even more preferably 100 to 300° C., particularly preferably 100 to 280° C.

Examples of the organic solvent (B) of the present invention include dihydric alcohol compounds and monohydric alcohol compounds. Examples of the dihydric alcohol compounds include:

dihydric alcohol compounds having a straight chain with 2 to 15 carbon atoms (preferably 3 to 12, more preferably 4 to 10 carbon atoms), such as 1,2-ethanediol, 1,2-propanediol, 1,3-propanediol, 1,2-butanediol, 1,3-butanediol, 1,4-butanediol, 2,3-butanediol, 1,2-pentanediol, 1,5-pentanediol, 2,4-pentanediol, 1,2-hexanediol, 2,5-hexanediol, diethylene glycol, triethylene glycol, tetraethylene glycol, polyethylene glycol (molecular weight: 200 to 600), dipropylene glycol, and polypropylene glycol;

dihydric alcohol compounds having a branched chain with 3 to 20 carbon atoms (preferably 4 to 15, more preferably 5 to 12 carbon atoms), such as 2-methyl-1,3-propanediol, 2-methyl-1,4-butanediol, 3-methyl-1,3-butanediol, 2-methyl-2,4-pentanediol, 3-methyl-1,5-pentanediol, 2,4-diethyl-1,5-pentanediol, and 2-ethyl-1,3-hexanediol; and dihydric alcohol compounds having a C6 to C14 aryl group, such as 3-benzyloxy-1,2-propanediol, 4-benzyloxy-1,2-butanediol, and 4-benzyloxy-1,3-butanediol.

Examples of the monohydric alcohol compounds include:

monohydric alcohol compounds having a C1 to C15 aliphatic group, such as methanol, ethanol, 1-propanol, 2-propanol, isopropanol, 1-butanol, 2-butanol, 1-heptanol, 2-heptanol, 3-heptanol, 1-hexanol, 2-hexanol, 3-hexanol, 2-methyl-1-pentanol, 3-methyl-1-pentanol, 4-methyl-1-pentanol, 2-methyl-2-pentanol, 2-methyl-3-pentanol, 2,2-dimethyl-1-butanol, 2-ethyl-1-butanol, ethylene glycol monomethyl ether, ethylene glycol monoethyl ether, propylene glycol monomethyl ether, propylene glycol monoethyl ether, ethylene glycol monobutyl ether, diethylene glycol monomethyl ether, diethylene glycol monoethyl ether, propylene glycol monopropyl ether, dipropylene glycol monoethyl ether, tripropylene glycol monomethyl ether, diethylene glycol monobutyl ether, triethylene glycol monomethyl ether, and polyethylene glycol monomethyl ether; and monohydric alcohol compounds having a C6 to C14 aryl group, such as ethylene glycol monobenzyl ether, ethylene glycol monophenyl ether, diethylene glycol monobenzyl ether, benzyl alcohol, 3-(benzyloxy)-1-propanol, 2-(benzyloxy)-1-butanol, and 5-(benzyloxy)-1-pentanol.

In view of compatibility with glass powder (A) and viscosity, preferred are dihydric alcohol compounds, more preferably dihydric alcohol compounds having a branched chain, even more preferably 2-methyl-1,3-propanediol, 2-methyl-1,4-butanediol, 3-methyl-1,3-butanediol, 2-methyl-2,4-pentanediol, 3-methyl-1,5-pentanediol, 2,4-diethyl-1,5-pentanediol, and 2-ethyl-1,3-hexanediol, particularly preferably 3-methyl-1,3-butanediol (boiling point: about 203° C., viscosity at 20° C.: about 250 mPa·s), 3-methyl-1,5-pentanediol (boiling point: about 250° C., viscosity at 20° C.: about 173 mPa·s), 2,4-diethyl-1,5-pentanediol (boiling point: about 264° C., viscosity at 20° C.: about 1,650 mPa·s), and 2-ethyl-1,3-hexanediol (boiling point: about 244° C., viscosity at 20° C.: about 271 mPa·s). The organic solvent (B) may be used alone, or two or more thereof may be used in an appropriate combination.

Running of the paste can be reduced to provide good ease of handling particularly when a paste-like dental glass composition of the present invention comprises a dihydric alcohol compound having a branched carbon structure. Though the reason for this remains unclear, the present inventors have proposed the following speculation. The presence of a branched chain with a predetermined number of carbon atoms in a dihydric alcohol compound provides moderate polarity, and this appears to improve the compatibility with the glass powder, or enable the maintenance of liquid properties with an appropriate viscosity and an appropriate boiling point, without causing solidification at ordinary temperature, even when the number of carbon atoms is increased. The paste, therefore, does not dry, and its runniness can be reduced when such a compound is mixed with the glass powder.

<Thickener (C)>

A paste-like dental glass composition of the present invention may further comprise a thickener (C), excluding an organic compound having three or more hydroxyl groups within the molecule. In a paste-like dental glass composition of the present invention, the thickener (C) can be minimized by containing the organic solvent (B). The thickener (C) may be used alone, or two or more thereof may be used in combination. The thickener (C) used in the present invention comprises at least one selected from the group consisting of an organic compound (C-1) having a viscosity at 20° C. of more than 2,500 mPa·s, an organic compound (C-2) that is solid at ordinary temperature, and an inorganic compound (C-3).

For the same reason described above, the thickener (C) is essentially free of an organic compound having three or more hydroxyl groups within the molecule. The content of an organic compound having three or more hydroxyl groups within the molecule may be, for example, 1,000 ppm or less by mass, preferably 100 ppm or less by mass, more preferably 10 ppm or less by mass, even more preferably 1 ppm or less by mass, particularly preferably 0.1 ppm or less by mass, most preferably 0 ppm by mass relative to the mass of the paste-like dental glass composition. Examples of organic compounds having three or more hydroxyl groups within the molecule include polysaccharide compound such as methyl cellulose, carboxycellulose, hydroxyethyl cellulose, xanthan gum, guar gum, carrageenan, tamarind seed gum, and pectin; sugar alcohol compounds such as sorbitol, erythritol, xylitol, and trehalose; and synthetic polyol compounds such as diglycerin, triglycerin, polyglycerin, and polyvinyl alcohol. A paste-like dental glass composition of the present invention is essentially free of an organic compound having three or more hydroxyl groups within the molecule, irrespective of an organic solvent or a thickener.

The organic compound (C-1) having a viscosity at 20° C. of more than 2,500 mPa·s used in the present invention (hereinafter, also referred to simply as "organic compound (C-1)") is not particularly limited, as long as a desirable viscosity increase can be achieved. Examples include radical polymerizable polyfunctional (meth)acrylates such as 2,2-bis[4-(3-acryloyloxy-2-hydroxypropoxy)phenyl]propane, 2,2-bis[4-(3-(methacryloyloxy-2-hydroxypropoxy)phenyl] propane (commonly known as "Bis-GMA"), and 2,2,4-trimethylhexamethylene bis(2-carbamoyloxyethyl)dimethacrylate (UDMA); and silicone oils such as dimethyl silicone oil, and methyl phenyl silicone oil. The upper limit of the viscosity of the organic compound (C-1) is not particularly limited. However, the viscosity at 20° C. may be 1,500,000 mPa·s or less because an excessively high viscosity may impair the burn-off process, such as by inhibiting the burn-off of organic solvent (B), or by impairing the burn-off of the thickener (C) itself, or may affect the shade after firing, or generate bubbles. The organic compound (C-1) has a viscosity at 20° C. of preferably 2,700 mPa·s or more, more preferably 2,900 mPa·s or more, even more preferably 3,000 mPa·s or more.

Examples of the organic compound (C-2) that is solid at ordinary temperature used in the present invention (hereinafter, also referred to simply as "organic compound (C-2)") include water-soluble polymeric compounds such as sodium polyacrylate, ammonium polyacrylate, polyethylene oxide, polyethylene glycol (molecular weight: 1,000 or more), and polyvinylpyrrolidone; and low-molecular fatty acid compounds. Examples of the fatty acid compounds include fatty acid metal salts having a fatty acid group with 10 to 30 carbon atoms (such as calcium stearate, magnesium stearate, zinc stearate, and aluminum stearate); fatty acid esters such as polyethylene glycol fatty acid esters (e.g., polyethylene glycol monostearate); fatty acids such as 12-hydroxystearic acid; and compounds having a fatty acid group with 8 to 30 carbon atoms, such as fatty acid amides (e.g., stearamide, oleamide, and ethylenebisoleamide). Preferred are compounds having a fatty acid group with 10 to 28 carbon atoms. The organic compound (C-2) comprises organic compounds that have no fluidity at ordinary temperature. The organic compound (C-2) also comprises a paste-like organic compound having fluidity, and slurry-like organic compounds having fluidity. However, organic compounds that are fluidic, and have a viscosity at 20° C. of 1,500,000 mPa·s or less are included in the organic compound (C-1).

The content of organic compound (C-1) or (C-2) can be reduced as small as possible by containing organic solvent (B). When the paste-like dental glass composition contains organic compound (C-1) or (C-2), the content of organic compound (C-1) or organic compound (C-2) is preferably 0.01 to 10 mass %, more preferably 0.05 to 8.0 mass %, even more preferably 0.1 to 6.0 mass % relative to the whole of the paste-like dental glass composition. When the content of organic compound (C-1) or organic compound (C-2) is 0.01 mass % or more, a thickening effect is produced that makes the paste less runny, and provides even better ease of handling. When the content of organic compound (C-1) or organic compound (C-2) is 10 mass % or less, it is possible to prevent the viscosity of the composition from becoming overly high, and moderately soft paste properties can be provided to enable easier application and facilitate a uniform build-up. When the paste-like dental glass composition contains both organic compound (C-1) and organic compound (C-2), it is preferable that the total content of organic compound (C-1) and organic compound (C-2) fall within the foregoing ranges. When the paste-like dental glass composition contains organic compound (C-1) or (C-2), it is preferable that the content of organic compound (C-1) or organic compound (C-2) (the total content of organic compound (C-1) and organic compound (C-2) when these are both contained) be smaller than the content of organic solvent (B) relative to the whole of the paste-like dental glass composition because adding a high-viscosity component in large amounts may impair the burn-off process such as by inhibiting the burn-off of organic solvent (B), or impairing the burn-off of the thickener (C) itself, or may affect the shade or generate bubbles.

Examples of the inorganic compound (C-3) used in the present invention include inorganic oxide particles (such as silica, alumina, titania, and zirconia) and composite oxide particles of these, calcium phosphate, hydroxyapatite, yttrium fluoride, ytterbium fluoride, smectite (magnesium aluminum silicate), bentonite, and water glass (sodium silicate aqueous solution). Preferred for use among these are particles of silica, alumina, and titania produced by flame pyrolysis, for example, such as Aerosil® OX50, Aerosil® 50, Aerosil® 130, Aerosil® 200, Aerosil® 380, Aerosil® MOX80, Aerosil® R972, Aerosil® RY50, Aeroxide® AluC, Aeroxide® $TiO_2$P25, VP Zirconium Oxide 3-YSZ, and VP Zirconium Oxide 3-YSZ PH manufactured by Nippon Aerosil Co., Ltd. More preferred for use are silica particles produced by flame pyrolysis, for example, such as the Aerosil® series manufactured by Nippon Aerosil Co., Ltd. under this trade name.

When the inorganic compound (C-3) is a particle, the particle may be one that is surface treated with a surface treatment agent. The surface treatment agent may be, for example, a silane coupling agent. The silane coupling agent is not particularly limited, and examples include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(2-methoxyethoxy)silane, 3,3,3-trifluoropropyltrimethoxysilane, methyl-3,3,3-trifluoropropyldimethoxysilane, 2-(3,4-epoxycyclohexyl)ethyltrimethoxysilane, 3-glycidoxypropyltrimethoxysilane, 3-glycidoxypropylmethyldiethoxysilane, 3-glycidoxypropyltriethoxysilane, 3-methacryloxypropylmethyldimethoxysilane, γ-methacryloxypropylmethyldiethoxysilane, N-β(aminoethyl)γ-aminopropylmethyldimethoxysilane, N-β(aminoethyl)γ-aminopropyltrimethoxysilane, N-β(aminoethyl)γ-aminopropyltriethoxysilane, 3-aminopropyltrimethoxysilane, 3-aminopropyltriethoxysilane, N-phenyl-γ-aminopropyltrimethoxysilane, 3-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloxyalkyltrimethoxysilane (3 to 12 carbon atoms between the (meth)acryloxy group and the silicon atom; e.g., γ-methacryloxypropyltrimethoxysilane), and ω-(meth)acryloxyalkyltriethoxysilane (3 to 12 carbon atoms between the (meth) acryloxy group and the silicon atom; e.g., γ-methacryloxypropyltriethoxysilane). The surface treatment agent may be used alone, or two or more thereof may be used in combination.

In view of uniform dispersibility in the composition, the particle has an average particle diameter of preferably 1 to 50 nm, more preferably 5 to 40 nm. The average particle diameter can be measured as a mean value of particle diameters of randomly selected 100 particles in an electron micrograph of particles. For non-spherical particles, the particle diameter is determined as an arithmetic mean value of the maximum and minimum lengths of filler particles. For agglomerated particles, the particle diameter is the diameter of a primary particle.

The particle shape is not particularly limited, and the particle may be used as a powder of irregularly shaped or spherical particles.

The content of inorganic compound (C-3) can be reduced as small as possible by containing organic solvent (B). When the paste-like dental glass composition contains inorganic compound (C-3), the content of inorganic compound (C-3) is preferably 0.001 to 10 mass %, more preferably 0.005 to 5.0 mass %, even more preferably 0.01 to 1.0 mass %, particularly preferably 0.05 to 0.4 mass % relative to the whole of the paste-like dental glass composition. When the content of inorganic compound (C-3) is 0.001 mass % or more, a thickening effect is produced that makes the paste less runny, and provides even better ease of handling. When the content of inorganic compound (C-3) is 10 mass % or less, it is possible to prevent the viscosity of the composition from becoming overly high, and moderately soft paste properties can be provided to enable easier application and facilitate a uniform build-up. There is also no possibility of causing prominent opacification after firing. When the paste-like dental glass composition contains inorganic compound (C-3), it is preferable that the content of inorganic compound (C-3) be smaller than the content of organic solvent (B) relative to the whole of the paste-like dental glass composition because the shade may be affected by specific components (such as Si, Al, and Ti), and the desired shade may not be obtained when the inorganic compound (C-3) is added in large amounts.

A paste-like dental glass composition of the present invention may comprise additional components (optional components) other than the glass powder (A), organic solvent (B), and thickener (C), provided that it does not hinder the effects of the present invention. Examples of such additional components include water, a colorant, a pH adjuster, a polymerization accelerator, and a polymerization initiator. The colorant may be amorphous or crystalline. The glass powder (A) may comprise a crystalline powder as a colorant. The colorant may be, for example, a colorant that decolors during firing. Examples of colorants that decolor during firing include food dyes that dissolve in organic solvent. Examples of the food dyes include:

- organic dyes containing two or more aromatic groups, such as yellow 4 (tartrazine), yellow 5 (sunset yellow FCF), red 2 (amaranth), red 102 (new coccin), blue 1 (brilliant blue FCF), blue 2 (indigo carmine), green 3 (fast green FCF), and red 102 (new coccin);
- organic dyes containing fused aromatic groups with a xanthene scaffold (xanthene dye), such as acid red 289, bromopyrogallol red, rhodamine B, rhodamine 6G, rhodamine 6GP, rhodamine 3GO, rhodamine 123, eosin (eosin B, eosin Y), fluorescein, and fluorescein isothiocyanate;
- cochineal dyes (carmic acid dyes); and
- betalain dyes such as beet red (main components: isobetanin and betanin), betanin, isobetanin, probetanin, and neobetanin.

A certain embodiment is, for example, a paste-like dental glass composition that comprises a glass powder (A), and an organic solvent (B) having two or less hydroxyl groups within the molecule and a viscosity at 20° C. of 2,500 mPa·s or less, and being essentially free of an organic compound having three or more hydroxyl groups within the molecule, and a colorant that decolors during firing. The definition of "essentially free of a colorant that decolors during firing" is the same as that described above in conjunction with the content of an organic solvent having three or more hydroxyl groups within the molecule. The content of the additional components is not particularly limited, and is preferably 15.0 mass % or less, more preferably 12.0 mass % or less.

A paste-like dental glass composition of the present invention can be used for the fabrication of dental prostheses such as ceramic inlays, onlays, laminate veneers, and crowns.

The frame that is the subject of a build-up of a paste-like dental glass composition of the present invention is not particularly limited, and may be, for example, a metal frame, or a ceramic frame (for example, a zirconia frame).

The uses of a paste-like dental glass composition of the present invention are not particularly limited, and a paste-like dental glass composition of the present invention can be used as, for example, body porcelain (dentin-color porcelain), cervical porcelain, incisal porcelain (enamel-color porcelain), translucent porcelain, opaque porcelain, or stain porcelain.

To prepare a dental prosthesis, a paste-like dental glass composition of the present invention is fired after build-up. The firing temperature (highest temperature in firing) can be appropriately varied according to factors such as the type of porcelain, or the form of use, and is not particularly limited, as long as the inorganic pigment can exhibit color. However, the firing temperature is preferably 700° C. or more, more preferably 730° C. or more, even more preferably 760° C. or more. The upper limit of firing temperature is not particularly limited, and is preferably 1,050° C. or less, more preferably 1,000° C. or less, even more preferably 980° C. or less. The rate of temperature increase to the highest temperature in firing can be appropriately varied according to the type of porcelain, and is not particularly limited. Preferably, the rate of temperature increase is about 10 to 70° C./min, more preferably about 20 to 60° C./min. A paste-like dental glass composition of the present invention may be dried after build-up and before firing. The drying conditions are not particularly limited. A paste-like dental glass composition of the present invention may be fired in a vacuum after build-up because vacuum firing enables a great reduction of bubbles present in the glass composition, and the dental prosthesis obtained can have even higher transparency and more superior aesthetics. The degree of vacuum in vacuum firing is not particularly limited, and may be 750 mmHg or less. The starting temperature for vacuuming is not particularly limited, and may be about 550 to 700° C.

An example of the preferred method of production of a paste-like dental glass composition of the present invention is a method comprising the step of mixing a glass powder (A) and an organic solvent (B). The mixing conditions are not particularly limited, and the components to be contained may be introduced at once, or may be separately introduced. A common mixer may be used for mixing. Examples include mortars, biaxial mixers (twin mixers), three-axis mixers (triple action mixers), kneaders, and planetary mixers. Preferred for use are mortars and planetary mixers.

A paste-like dental glass composition of the present invention, in use, has a paste form to enable a build-up. Accordingly, for example, a paste-like dental glass composition of the present invention may be provided as a dental porcelain kit comprising a liquid component (a first agent) containing an organic solvent (B), and a powder component (a second agent) containing a glass powder (A), and may be used as a paste-like dental glass composition by a user mixing the first agent and the second agent immediately before use. In such a kit form, factors such as the types, contents, and boiling points of the components (A) and (B) may be varied as appropriate, and changes such as additions and deletions of any components are possible based on the above descriptions.

Another embodiment of the present invention may be, for example, use of a paste-like dental glass composition comprising a glass powder (A) and an organic solvent (B) for the treatment of teeth (for example, aesthetic dental treatments, treatments of missing teeth, prosthetic restorative treatments using prosthetic devices such as artificial teeth, and treatments of dental caries).

In all of the foregoing embodiments, aspects such as the type, content and boiling point of each component can be changed as appropriate, and changes such as additions and deletions can be made in any of the components based on the above descriptions. In all of the foregoing embodiments, the composition and property values of the paste-like dental glass compositions can be varied and combined as appropriate.

The present invention encompasses embodiments combining the foregoing features, provided that the present invention can exhibit its effects with such combinations made in various forms within the technical idea of the present invention.

EXAMPLES

The following describes the present invention in greater detail by way of EXAMPLES. It is to be noted, however, that the present invention is in no way limited by the following EXAMPLES, and various changes may be made by a person with ordinary skill in the art within the technical idea of the present invention.

Examples 1 to 27 and Comparative Examples 1 to 7

Paste-like dental glass compositions were prepared for Examples and Comparative Examples, and their properties were evaluated as follows. The results are presented in Tables 2 and 3.

[Preparation of Paste-Like Dental Glass Composition]

Glass powders (A-1), (A-2), and (A-3) and a commercially available product Cerabien® ZR External Stain Red (manufactured by Kuraray Noritake Dental Inc.) were used as glass powders (A). Glass powders (A-1), (A-2), and (A-3) were prepared by pulverizing glass obtained after heat treatment and cooling of a mixture prepared by mixing the raw material components in the proportions (unit: mass %) shown in Table 1.

TABLE 1

| Components | (A-1) | (A-2) | (A-3) |
|---|---|---|---|
| $SiO_2$ | 65.3 | 68.6 | 63.3 |
| $Al_2O_3$ | 6.8 | 6.4 | 7.4 |
| CaO | 1.2 | 1.1 | 1.2 |
| $K_2O$ | 5.4 | 5.3 | 5.5 |
| $Na_2O$ | 4.6 | 3.6 | 5.3 |
| $B_2O_3$ | 15.9 | 14.2 | 16.5 |
| ZnO | 0.8 | 0.8 | 0.8 |

The glass powder (A) was mixed with the components shown in Table 2 or 3, in the mass percentages provided in Table 2 or 3. These were mixed in a mortar under ordinary temperature for about 10 minutes to prepare paste-like dental glass compositions. The following components were used.

[Organic Solvent (B)]

3-Methyl-1,3-butanediol: manufactured by Kuraray Co., Ltd.; boiling point: about 203° C., viscosity at 20° C.: about 250 mPa·s 3-Methyl-1,5-pentanediol: manufactured by Kuraray Co., Ltd.; boiling point: about 250° C., viscosity at 20° C.: about 173 mPa·s 2,4-Diethyl-1,5-pentanediol: manufactured by Tokyo Chemical Industry Co., Ltd.; boiling point: about 264° C., viscosity at 20° C.: about 1,650 mPa·s 2-Ethyl-1,3-hexanediol: manufactured by Tokyo Chemical Industry Co., Ltd.; boiling point: about 244° C., viscosity at 20° C.: about 271 mPa·s 1,3-Butanediol: manufactured by Tokyo Chemical Industry Co., Ltd.; boiling point: about 207° C., viscosity at 20° C.: about 96 mPa·s 1,4-Butanediol: manufactured by Tokyo Chemical Industry Co., Ltd.; boiling point: about 235° C., viscosity at 20° C.: about 85 mPa·s 1,5-Pentanediol: manufactured by Tokyo Chemical Industry Co., Ltd.; boiling point: about 239° C., viscosity at 20° C.: about 128 mPa·s 1,2-Hexanediol: manufactured by Tokyo Chemical Industry Co., Ltd.; boiling point: about 222° C., viscosity at 20° C.: about 87 mPa·s Polyethylene glycol (molecular weight 200): manufactured by Tokyo Chemical Industry Co., Ltd.; boiling point: about 250° C. (decomposes at 220° C.), viscosity at 20° C.: about 65 mPa·s Ethylene glycol monobenzyl ether: manufactured by Tokyo Chemical Industry Co., Ltd.; boiling point: about 244° C., viscosity at 20° C.: about 41 mPa·s Ethylene glycol monophenyl ether: manufactured by Tokyo Chemical Industry Co., Ltd.; boiling point: about 244° C., viscosity at 20° C.: about 29 mPa·s Triethylene glycol monomethyl ether: manufactured by Tokyo Chemical Industry Co., Ltd.; boiling point: about 248° C., viscosity at 20° C.: about 8 mPa·s

[Thickener (C)]

Bis-GMA: Sigma-Aldrich Japan; viscosity at 20° C.: about 100,000 mPa·s 12-Hydroxystearic acid: manufactured by Tokyo Chemical Industry Co., Ltd., white solid Aerosil® R976S: manufactured by Nippon Aerosil Co., Ltd., hydrophobic particulate silica, white powder Aerosil® 300: manufactured by Nippon Aerosil Co., hydrophilic particulate silica, white powder

[Organic Solvents Other than Organic Solvent (B)]

Glycerin: manufactured by Tokyo Chemical Industry Co., Ltd.; boiling point: about 290° C., viscosity at 20° C.: about 1,412 mPa·s 1,2,4-Butanetriol: manufactured by Tokyo Chemical Industry Co., Ltd.; boiling point: about 312° C.

1,2,3-Butanetriol: manufactured by Tokyo Chemical Industry Co., Ltd.; boiling point: about 305° C.

1,2,6-Hexanetriol: manufactured by Tokyo Chemical Industry Co., Ltd.; boiling point: about 345° C., viscosity at 20° C.: 2,460 mPa·s

[Thickeners Other than Thickener (C)]

Xanthan gum: manufactured by Tokyo Chemical Industry Co., Ltd., pale yellow solid Methyl cellulose: manufactured by Tokyo Chemical Industry Co., Ltd., white solid

[Other]

Purified water: manufactured by KENEI Pharmaceutical Co., Ltd.; boiling point: about 100° C., viscosity at 20° C.: about 1 mPa·s (1) Measurement Methods of Glass Transition Temperature and Softening Point of Glass Powder (A)

The glass transition temperature and softening point were determined from a thermal expansion curve by taking measurements with a thermomechanical analyzer TMA8311 (manufactured by Rigaku Corporation; measurements were made at a rate of temperature increase of 10° C./min and using compression loading) in compliance with JIS T 6526: 2018 (n=3). The mean values were used as glass transition temperatures and softening points.

(2) Measurement Method of Paste Viscosity

The paste-like dental glass composition prepared above was measured for viscosity under ordinary temperature at 20 rpm, using a B-type viscometer (Brookfield viscometer), and the mean value was calculated (n=3). The preferred paste viscosity is 2,000 to 80,000 mPa·s, more preferably 3,500 to 65,000 mPa·s, even more preferably 5,000 to 55,000 mPa·s, particularly preferably 7,000 to 45,000 mPa·s.

(3) Measurement Method of Paste Runniness

The paste-like dental glass composition prepared (500±10 mg) was placed on a glass plate, and the distance (mm) traveled by the paste was measured after the glass plate was vertically held for 90 seconds. The mean value was calculated (n=3). The preferred paste runniness is 80 mm or less, more preferably 40 mm or less, even more preferably 10 mm or less, particularly preferably 5 mm or less.

(4) Method of Discoloration Evaluation after Firing, and Method of Appearance Evaluation after Firing The paste-like dental glass composition prepared above was built up into a zirconia plate measuring 10 mm in length and 35 mm in width, and fired under the firing conditions shown in Tables 2 and 3 to obtain a sintered body. The color of the sintered body was then visually checked for discoloration (n=3). The sintered body was evaluated as "Good" when discoloration was not observed in any of its specimens (black or grey discoloration, for example), and "Moderate" when discoloration was observed in any one of the specimens.

The appearance of the sintered body was evaluated using the following criteria (n=3). For example, the sintered body was evaluated as "Good" when all of its specimens satisfied the condition for this category, and "Moderate" when any one of the specimens was "Moderate".

<Evaluation Criteria>

Good: Showing a transparent look and firing is sufficient, or showing a sufficient color when a pigment is added Moderate: Appearing slightly less transparent, or showing a slightly reduced color when a pigment is added Poor: No transparent look and failed firing, or showing no color when a pigment is added Black or grey discoloration due to the organic materials was visible after firing in Comparative Examples 1 to 5 containing organic solvents having three or more hydroxyl groups within the molecule, and in Comparative Examples 6 and 7 containing thickeners having three or more hydroxyl groups within the molecule. In contrast, no discoloration was observed in Examples 1 to 27. In Examples 1 to 27, the paste had reduced runniness and the paste viscosity was desirable, confirming that the paste has good ease of handling in a build-up procedure.

TABLE 2

| Components (mass %) | | Example No 1 | 2 | 3 | 4 | 5 | 6 | 7 | 8 |
|---|---|---|---|---|---|---|---|---|---|
| Glass powder (A) | (A-1) | 67.0 | 0.0 | 0.0 | 0.0 | 67.0 | 67.0 | 67.0 | 67.0 |
| | (A-2) | 0.0 | 67.0 | 0.0 | 0.0 | 0.0 | 0.0 | 0.0 | 0.0 |
| | (A-3) | 0.0 | 0.0 | 67.0 | 0.0 | 0.0 | 0.0 | 0.0 | 0.0 |
| | Cerabien ZR External Stain Red | 0.0 | 0.0 | 0.0 | 67.0 | 0.0 | 0.0 | 0.0 | 0.0 |

TABLE 2-continued

| | | | | | | | | | | |
|---|---|---|---|---|---|---|---|---|---|---|
| Organic solvent (B) | 3-Methyl-1,3-butanediol | | 33.0 | 33.0 | 33.0 | 33.0 | 0.0 | 0.0 | 0.0 | 0.0 |
| | 3-Methyl-1,5-pentanediol | | 0.0 | 0.0 | 0.0 | 0.0 | 33.0 | 0.0 | 0.0 | 0.0 |
| | 2,4-Diethyl-1,5-pentanediol | | 0.0 | 0.0 | 0.0 | 0.0 | 0.0 | 33.0 | 0.0 | 0.0 |
| | 2-Ethyl-1,3-hexanediol | | 0.0 | 0.0 | 0.0 | 0.0 | 0.0 | 0.0 | 33.0 | 0.0 |
| | 1,3-Butanediol | | 0.0 | 0.0 | 0.0 | 0.0 | 0.0 | 0.0 | 0.0 | 33.0 |
| | 1,4-Butanediol | | 0.0 | 0.0 | 0.0 | 0.0 | 0.0 | 0.0 | 0.0 | 0.0 |
| | 1,5-Pentanediol | | 0.0 | 0.0 | 0.0 | 0.0 | 0.0 | 0.0 | 0.0 | 0.0 |
| | 1,2-Hexanediol | | 0.0 | 0.0 | 0.0 | 0.0 | 0.0 | 0.0 | 0.0 | 0.0 |
| | Polyethylene glycol (molecular weight 200) | | 0.0 | 0.0 | 0.0 | 0.0 | 0.0 | 0.0 | 0.0 | 0.0 |
| | Ethylene glycol monobenzyl ether | | 0.0 | 0.0 | 0.0 | 0.0 | 0.0 | 0.0 | 0.0 | 0.0 |
| | Ethylene glycol monophenyl ether | | 0.0 | 0.0 | 0.0 | 0.0 | 0.0 | 0.0 | 0.0 | 0.0 |
| | Triethylene glycol monomethyl ether | | 0.0 | 0.0 | 0.0 | 0.0 | 0.0 | 0.0 | 0.0 | 0.0 |
| Thickener (C) | (C-1) | Bis-GMA | 0.0 | 0.0 | 0.0 | 0.0 | 0.0 | 0.0 | 0.0 | 0.0 |
| | (C-2) | 12-Hydroxystearic acid | 0.0 | 0.0 | 0.0 | 0.0 | 0.0 | 0.0 | 0.0 | 0.0 |
| | (C-3) | Aerosil ® R976S | 0.0 | 0.0 | 0.0 | 0.0 | 0.0 | 0.0 | 0.0 | 0.0 |
| | | Aerosil ® 300 | 0.0 | 0.0 | 0.0 | 0.0 | 0.0 | 0.0 | 0.0 | 0.0 |
| Organic solvents other than (B) | Glycerin | | 0.0 | 0.0 | 0.0 | 0.0 | 0.0 | 0.0 | 0.0 | 0.0 |
| | 1,2,4-Butanetriol | | 0.0 | 0.0 | 0.0 | 0.0 | 0.0 | 0.0 | 0.0 | 0.0 |
| | 1,2,3-Butanetriol | | 0.0 | 0.0 | 0.0 | 0.0 | 0.0 | 0.0 | 0.0 | 0.0 |
| | 1,2,6-Hexanetriol | | 0.0 | 0.0 | 0.0 | 0.0 | 0.0 | 0.0 | 0.0 | 0.0 |
| Thickeners other than (C) (carbohydrates) | Xanthan gum | | 0.0 | 0.0 | 0.0 | 0.0 | 0.0 | 0.0 | 0.0 | 0.0 |
| | Methyl cellulose | | 0.0 | 0.0 | 0.0 | 0.0 | 0.0 | 0.0 | 0.0 | 0.0 |
| Other | Purified water | | 0.0 | 0.0 | 0.0 | 0.0 | 0.0 | 0.0 | 0.0 | 0.0 |

| | | | Example No | | | | | | | |
|---|---|---|---|---|---|---|---|---|---|---|
| Components (mass %) | | | 9 | 10 | 11 | 12 | 13 | 14 | 15 | 16 |
| Glass powder (A) | (A-1) | | 0.0 | 67.0 | 67.0 | 67.0 | 67.0 | 67.0 | 67.0 | 67.0 |
| | (A-2) | | 0.0 | 0.0 | 0.0 | 0.0 | 0.0 | 0.0 | 0.0 | 0.0 |
| | (A-3) | | 0.0 | 0.0 | 0.0 | 0.0 | 0.0 | 0.0 | 0.0 | 0.0 |
| | Cerabien ZR External Stain Red | | 67.0 | 0.0 | 0.0 | 0.0 | 0.0 | 0.0 | 0.0 | 0.0 |
| Organic solvent (B) | 3-Methyl-1,3-butanediol | | 0.0 | 0.0 | 0.0 | 0.0 | 0.0 | 28.0 | 28.0 | 28.0 |
| | 3-Methyl-1,5-pentanediol | | 0.0 | 0.0 | 0.0 | 0.0 | 0.0 | 0.0 | 0.0 | 0.0 |
| | 2,4-Diethyl-1,5-pentanediol | | 0.0 | 0.0 | 0.0 | 0.0 | 0.0 | 0.0 | 0.0 | 0.0 |
| | 2-Ethyl-1,3-hexanediol | | 0.0 | 0.0 | 0.0 | 0.0 | 0.0 | 0.0 | 0.0 | 0.0 |
| | 1,3-Butanediol | | 33.0 | 0.0 | 0.0 | 0.0 | 0.0 | 0.0 | 0.0 | 0.0 |
| | 1,4-Butanediol | | 0.0 | 33.0 | 0.0 | 0.0 | 0.0 | 0.0 | 0.0 | 0.0 |
| | 1,5-Pentanediol | | 0.0 | 0.0 | 33.0 | 0.0 | 0.0 | 0.0 | 0.0 | 0.0 |
| | 1,2-Hexanediol | | 0.0 | 0.0 | 0.0 | 33.0 | 0.0 | 0.0 | 0.0 | 0.0 |
| | Polyethylene glycol (molecular weight 200) | | 0.0 | 0.0 | 0.0 | 0.0 | 33.0 | 0.0 | 0.0 | 0.0 |
| | Ethylene glycol monobenzyl ether | | 0.0 | 0.0 | 0.0 | 0.0 | 0.0 | 5.0 | 0.0 | 0.0 |
| | Ethylene glycol monophenyl ether | | 0.0 | 0.0 | 0.0 | 0.0 | 0.0 | 0.0 | 5.0 | 0.0 |
| | Triethylene glycol monomethyl ether | | 0.0 | 0.0 | 0.0 | 0.0 | 0.0 | 0.0 | 0.0 | 5.0 |
| Thickener (C) | (C-1) | Bis-GMA | 0.0 | 0.0 | 0.0 | 0.0 | 0.0 | 0.0 | 0.0 | 0.0 |
| | (C-2) | 12-Hydroxystearic acid | 0.0 | 0.0 | 0.0 | 0.0 | 0.0 | 0.0 | 0.0 | 0.0 |
| | (C-3) | Aerosil ® R976S | 0.0 | 0.0 | 0.0 | 0.0 | 0.0 | 0.0 | 0.0 | 0.0 |
| | | Aerosil ® 300 | 0.0 | 0.0 | 0.0 | 0.0 | 0.0 | 0.0 | 0.0 | 0.0 |
| Organic solvents other than (B) | Glycerin | | 0.0 | 0.0 | 0.0 | 0.0 | 0.0 | 0.0 | 0.0 | 0.0 |
| | 1,2,4-Butanetriol | | 0.0 | 0.0 | 0.0 | 0.0 | 0.0 | 0.0 | 0.0 | 0.0 |
| | 1,2,3-Butanetriol | | 0.0 | 0.0 | 0.0 | 0.0 | 0.0 | 0.0 | 0.0 | 0.0 |
| | 1,2,6-Hexanetriol | | 0.0 | 0.0 | 0.0 | 0.0 | 0.0 | 0.0 | 0.0 | 0.0 |
| Thickeners other than (C) (carbohydrates) | Xanthan gum | | 0.0 | 0.0 | 0.0 | 0.0 | 0.0 | 0.0 | 0.0 | 0.0 |
| | Methyl cellulose | | 0.0 | 0.0 | 0.0 | 0.0 | 0.0 | 0.0 | 0.0 | 0.0 |
| Other | Purified water | | 0.0 | 0.0 | 0.0 | 0.0 | 0.0 | 0.0 | 0.0 | 0.0 |

TABLE 2-continued

| | Example No | | | | | | | |
|---|---|---|---|---|---|---|---|---|
| | 1 | 2 | 3 | 4 | 5 | 6 | 7 | 8 |
| Glass transition temperature of glass powder (A) [° C.] | 470 | 482 | 455 | 540 | 470 | 470 | 470 | 470 |
| Softening point of glass powder (A) [° C.] | 560 | 558 | 554 | 615 | 560 | 560 | 560 | 560 |
| Paste viscosity [mPa · s] | 8500 | 9000 | 8500 | 12000 | 7500 | 35500 | 9000 | 4000 |
| Paste runniness [mm] | 1.0 | 1.0 | 1.0 | 1.5 | 3.0 | 0.5 | 1.0 | 30 |
| Firing temperature [° C.] * | 760 | 760 | 760 | 760 | 760 | 760 | 760 | 760 |
| Presence or absence of discoloration after firing (e.g., black or grey discoloration) | Absent | Absent | Absent | Absent | Absent | Absent | Absent | Absent |
| Appearance evaluation after firing | Good | Good | Good | Moderate | Good | Good | Good | Good |

| | Example No | | | | | | | |
|---|---|---|---|---|---|---|---|---|
| | 9 | 10 | 11 | 12 | 13 | 14 | 15 | 16 |
| Glass transition temperature of glass powder (A) [° C.] | 540 | 470 | 470 | 470 | 470 | 470 | 470 | 470 |
| Softening point of glass powder (A) [° C.] | 615 | 560 | 560 | 560 | 560 | 560 | 560 | 560 |
| Paste viscosity [mPa · s] | 4500 | 3500 | 4500 | 4000 | 2500 | 8500 | 8500 | 8000 |
| Paste runniness [mm] | 21 | 35 | 20 | 32 | 58 | 1.0 | 1.0 | 1.5 |
| Firing temperature [° C.] * | 760 | 760 | 760 | 760 | 760 | 760 | 760 | 760 |
| Presence or absence of discoloration after firing (e.g., black or grey discoloration) | Absent | Absent | Absent | Absent | Absent | Absent | Absent | Absent |
| Appearance evaluation after firing | Moderate | Good | Good | Good | Good | Good | Good | Good |

* In the table, "Firing temperature" means the highest temperature in firing.

Conditions other than firing temperature: Drying time: 6 minutes, starting temperature for firing: 400° C., rate of temperature increase: 45° C./min, staring temperature for vacuuming: 650° C., degree of vacuum: 720 mmHg, rapid cooling to room temperature

TABLE 3

| Components (mass %) | | 17 | 18 | 19 | 20 | 21 | 22 | 23 | 24 | 25 | 26 | 27 |
|---|---|---|---|---|---|---|---|---|---|---|---|---|
| | | Example No | | | | | | | | | | |
| Glass powder (A) | (A-1) | 67.0 | 67.0 | 67.0 | 66.6 | 62.0 | 66.6 | 62.0 | 66.6 | 62.0 | 66.6 | 66.6 |
| | (A-2) | 0.0 | 0.0 | 0.0 | 0.0 | 0.0 | 0.0 | 0.0 | 0.0 | 0.0 | 0.0 | 0.0 |
| | (A-3) | 0.0 | 0.0 | 0.0 | 0.0 | 0.0 | 0.0 | 0.0 | 0.0 | 0.0 | 0.0 | 0.0 |
| | Cerabien ZR External Stain Red | 0.0 | 0.0 | 0.0 | 0.0 | 0.0 | 0.0 | 0 | 0.0 | 0.0 | 0.0 | 0.0 |
| Organic solvent (B) | 3-Methyl-1,3-butanediol | 28.0 | 32.6 | 32.0 | 33.0 | 33.0 | 33.0 | 33.0 | 0.0 | 0.0 | 28.0 | 28.0 |
| | 3-Methyl-1,5-pentanediol | 0.0 | 0.0 | 0.0 | 0.0 | 0.0 | 0.0 | 0.0 | 0.0 | 0.0 | 0.0 | 0.0 |
| | 2,4-Diethyl-1,5-pentanediol | 0.0 | 0.0 | 0.0 | 0.0 | 0.0 | 0.0 | 0.0 | 0.0 | 0.0 | 0.0 | 0.0 |
| | 2-Ethyl-1,3-hexanediol | 0.0 | 0.0 | 0.0 | 0.0 | 0.0 | 0.0 | 0.0 | 0.0 | 0.0 | 0.0 | 0.0 |
| | 1,3-Butanediol | 0.0 | 0.0 | 0.0 | 0.0 | 0.0 | 0.0 | 0.0 | 33.0 | 33.0 | 0.0 | 0.0 |
| | 1,4-Butanediol | 0.0 | 0.0 | 0.0 | 0.0 | 0.0 | 0.0 | 0.0 | 0.0 | 0.0 | 0.0 | 0.0 |
| | 1,5-Pentanediol | 0.0 | 0.0 | 0.0 | 0.0 | 0.0 | 0.0 | 0.0 | 0.0 | 0.0 | 0.0 | 0.0 |
| | 1,2-Hexanediol | 0.0 | 0.0 | 0.0 | 0.0 | 0.0 | 0.0 | 0.0 | 0.0 | 0.0 | 0.0 | 0.0 |
| | Polyethylene glycol (molecular weight 200) | 0.0 | 0.0 | 0.0 | 0.0 | 0.0 | 0.0 | 0.0 | 0.0 | 0.0 | 0.0 | 0.0 |
| | Ethylene glycol monobenzyl ether | 0.0 | 0.0 | 0.0 | 0.0 | 0.0 | 0.0 | 0.0 | 0.0 | 0.0 | 0.0 | 0.0 |
| | Ethylene glycol monophenyl ether | 0.0 | 0.0 | 0.0 | 0.0 | 0.0 | 0.0 | 0.0 | 0.0 | 0.0 | 0.0 | 0.0 |
| | Triethylene glycol monomethyl ether | 0.0 | 0.0 | 0.0 | 0.0 | 0.0 | 0.0 | 0.0 | 0.0 | 0.0 | 0.0 | 0.0 |
| Thickener (C) | (C-1) Bis-GMA | 5.0 | 0.0 | 0.0 | 0.0 | 0.0 | 0.0 | 0.0 | 0.0 | 0.0 | 0.0 | 0.0 |
| | (C-2) 12-Hydroxystearic acid | 0.0 | 0.40 | 1.0 | 0.0 | 0.0 | 0.0 | 0.0 | 0.0 | 0.0 | 0.0 | 0.40 |
| | (C-3) Aerosil ® R976S | 0.0 | 0.0 | 0.0 | 0.40 | 5.0 | 0.0 | 0.0 | 0.40 | 5.0 | 0.40 | 0.0 |
| | Aerosil ® 300 | 0.0 | 0.0 | 0.0 | 0.0 | 0.0 | 0.40 | 5.0 | 0.0 | 0.0 | 0.0 | 0.0 |
| Organic solvents other than (B) | Glycerin | 0.0 | 0.0 | 0.0 | 0.0 | 0.0 | 0.0 | 0.0 | 0.0 | 0.0 | 0.0 | 0.0 |
| | 1,2,4-Butanetriol | 0.0 | 0.0 | 0.0 | 0.0 | 0.0 | 0.0 | 0.0 | 0.0 | 0.0 | 0.0 | 0.0 |
| | 1,2,3-Butanetriol | 0.0 | 0.0 | 0.0 | 0.0 | 0.0 | 0.0 | 0.0 | 0.0 | 0.0 | 0.0 | 0.0 |
| | 1,2,6-Hexanetriol | 0.0 | 0.0 | 0.0 | 0.0 | 0.0 | 0.0 | 0.0 | 0.0 | 0.0 | 0.0 | 0.0 |
| Thickeners other than (C) (carbohydrates) | Xanthan gum | 0.0 | 0.0 | 0.0 | 0.0 | 0.0 | 0.0 | 0.0 | 0.0 | 0.0 | 0.0 | 0.0 |
| | Methyl cellulose | 0.0 | 0.0 | 0.0 | 0.0 | 0.0 | 0.0 | 0.0 | 0.0 | 0.0 | 0.0 | 0.0 |
| Other | Purified water | 0.0 | 0.0 | 0.0 | 0.0 | 0.0 | 0.0 | 0.0 | 0.0 | 0.0 | 5.0 | 5.0 |

| Components (mass %) | | 1 | 2 | 3 | 4 | 5 | 6 | 7 |
|---|---|---|---|---|---|---|---|---|
| | | Comparative Example No | | | | | | |
| Glass powder (A) | (A-1) | 67.0 | 67.0 | 61.0 | 61.0 | 67.0 | 60.0 | 60.0 |
| | (A-2) | 0.0 | 0.0 | 0.0 | 0.0 | 0.0 | 0.0 | 0.0 |
| | (A-3) | 0.0 | 0.0 | 0.0 | 0.0 | 0.0 | 0.0 | 0.0 |
| | Cerabien ZR External Stain Red | 0.0 | 0.0 | 0.0 | 0.0 | 0.0 | 0.0 | 0.0 |
| Organic solvent (B) | 3-Methyl-1,3-butanediol | 0.0 | 10.0 | 0.0 | 0.0 | 0.0 | 0.0 | 0.0 |
| | 3-Methyl-1,5-pentanediol | 0.0 | 0.0 | 0.0 | 0.0 | 0.0 | 0.0 | 0.0 |
| | 2,4-Diethyl-1,5-pentanediol | 0.0 | 0.0 | 0.0 | 0.0 | 0.0 | 0.0 | 0.0 |
| | 2-Ethyl-1,3-hexanediol | 0.0 | 0.0 | 0.0 | 0.0 | 0.0 | 0.0 | 0.0 |
| | 1,3-Butanediol | 0.0 | 0.0 | 0.0 | 0.0 | 0.0 | 0.0 | 0.0 |
| | 1,4-Butanediol | 0.0 | 0.0 | 0.0 | 0.0 | 0.0 | 0.0 | 0.0 |
| | 1,5-Pentanediol | 0.0 | 0.0 | 0.0 | 0.0 | 0.0 | 0.0 | 0.0 |
| | 1,2-Hexanediol | 0.0 | 0.0 | 0.0 | 0.0 | 0.0 | 0.0 | 0.0 |
| | Polyethylene glycol (molecular weight 200) | 0.0 | 0.0 | 0.0 | 0.0 | 0.0 | 0.0 | 0.0 |

TABLE 3-continued

| | | | | | | | | |
|---|---|---|---|---|---|---|---|---|
| | Ethylene glycol monobenzyl ether | 0.0 | 0.0 | 0.0 | 0.0 | 0.0 | 0.0 | 0.0 |
| | Ethylene glycol monophenyl ether | 0.0 | 0.0 | 0.0 | 0.0 | 0.0 | 0.0 | 0.0 |
| | Triethylene glycol monomethyl ether | 0.0 | 0.0 | 0.0 | 0.0 | 0.0 | 0.0 | 0.0 |
| Thickener (C) | (C-1) Bis-GMA | 0.0 | 0.0 | 0.0 | 0.0 | 0.0 | 0.0 | 0.0 |
| | (C-2) 12-Hydroxystearic acid | 0.0 | 0.0 | 0.0 | 0.0 | 0.0 | 0.0 | 0.0 |
| | (C-3) Aerosil ® R976S | 0.0 | 0.0 | 0.0 | 0.0 | 0.0 | 0.0 | 0.0 |
| | Aerosil ® 300 | 0.0 | 0.0 | 0.0 | 0.0 | 0.0 | 0.0 | 0.0 |
| Organic solvents other than (B) | Glycerin | 33.0 | 23.0 | 0.0 | 0.0 | 0.0 | 0.0 | 0.0 |
| | 1,2,4-Butanetriol | 0.0 | 0.0 | 39.0 | 0.0 | 0.0 | 0.0 | 0.0 |
| | 1,2,3-Butanetriol | 0.0 | 0.0 | 0.0 | 39.0 | 0.0 | 0.0 | 0.0 |
| | 1,2,6-Hexanetriol | 0.0 | 0.0 | 0.0 | 0.0 | 33.0 | 0.0 | 0.0 |
| Thickeners other than (C) (carbohydrates) | Xanthan gum | 0.0 | 0.0 | 0.0 | 0.0 | 0.0 | 5.0 | 0.0 |
| | Methyl cellulose | 0.0 | 0.0 | 0.0 | 0.0 | 0.0 | 0.0 | 5.0 |
| Other | Purified water | 0.0 | 0.0 | 0.0 | 0.0 | 0.0 | 35.0 | 35.0 |

| | Example No | | | | | | | | | | |
|---|---|---|---|---|---|---|---|---|---|---|---|
| | 17 | 18 | 19 | 20 | 21 | 22 | 23 | 24 | 25 | 26 | 27 |
| Glass transition temperature of glass powder (A) [° C.] | 470 | 470 | 470 | 470 | 470 | 470 | 470 | 470 | 470 | 470 | 470 |
| Softening point of glass powder (A) [° C.] | 560 | 560 | 560 | 560 | 560 | 560 | 560 | 560 | 560 | 560 | 560 |
| Paste viscosity [mPa · s] | 30000 | 36500 | 42000 | 14500 | 28000 | 18500 | 36500 | 6000 | 12000 | 30500 | 37000 |
| Paste runniness [mm] | 0.5 | 0.5 | 0.5 | 0.5 | 0.5 | 0.5 | 0.5 | 10 | 3.0 | 0.5 | 0.5 |
| Firing temperature [° C.] * | 760 | 760 | 760 | 760 | 760 | 760 | 760 | 760 | 760 | 760 | 760 |
| Presence or absence of discoloration after firing (e.g., black or grey discoloration) | Absent | Absent | Absent | Absent | Absent | Absent | Absent | Absent | Absent | Absent | Absent |
| Appearance evaluation after firing | Good | Good | Good | Good | Moderate | Good | Moderate | Good | Moderate | Good | Good |

| | Comparative Example No | | | | | | |
|---|---|---|---|---|---|---|---|
| | 1 | 2 | 3 | 4 | 5 | 6 | 7 |
| Glass transition temperature of glass powder (A) [° C.] | 470 | 470 | 470 | 470 | 470 | 470 | 470 |
| Softening point of glass powder (A) [° C.] | 560 | 560 | 560 | 560 | 560 | 560 | 560 |
| Paste viscosity [mPa · s] | 44500 | 34000 | 43000 | 43000 | 44000 | 10500 | 12000 |
| Paste runniness [mm] | 1.0 | 1.5 | 1.0 | 1.0 | 1.0 | 1.0 | 1.0 |
| Firing temperature [° C.] * | 760 | 760 | 760 | 760 | 760 | 760 | 760 |
| Presence or absence of discoloration after firing (e.g., black or grey discoloration) | Blackening | Blackening | Blackening | Blackening | Blackening | Greying | Greying |
| Appearance evaluation after firing | | | | | | | |

* In the table, "Firing temperature" means the highest temperature in firing.

Conditions other than firing temperature: Drying time: 6 minutes, starting temperature for firing: 400° C., rate of temperature increase: 45° C./min, staring temperature for vacuuming: 650° C., degree of vacuum: 720 mmHg, rapid cooling to room temperature

INDUSTRIAL APPLICABILITY

With a paste-like dental glass composition of the present invention, a build-up procedure is easy because of reduced paste runniness and good ease of handling. A paste-like dental glass composition of the present invention is useful given an expected increase in the use of dental porcelain, particularly in response to the continuously growing demand for ceramic crowns and the associated increase in individual demand for better aesthetics.

The invention claimed is:

1. A paste-like dental glass composition comprising a glass powder (A), and an organic solvent (B) that is a dihydric alcohol compound having a C4 to C20 branched chain and that has a viscosity at 20° C. of 2,500 mPa·s or less, and being essentially free of an organic compound having three or more hydroxyl groups within the molecule.

2. The paste-like dental glass composition according to claim 1, which further comprises a thickener (C), the thickener (C) comprising at least one selected from the group consisting of an organic compound (C-1) having a viscosity at 20° C. of more than 2,500 mPa·s, an organic compound (C-2) that is solid at ordinary temperature, and an inorganic compound (C-3).

3. The paste-like dental glass composition according to claim 1, wherein the organic solvent (B) is a dihydric alcohol compound.

4. The paste-like dental glass composition according to claim 1, wherein the dihydric alcohol compound having a C4 to C20 branched chain comprises at least one selected from the group consisting of 2-methyl-1,3-propanediol, 2-methyl-1,4-butanediol, 3-methyl-1,3-butanediol, 2-methyl-2,4-pentanediol, 3-methyl-1,5-pentanediol, 2,4-diethyl-1,5-pentanediol, and 2-ethyl-1,3-hexanediol.

5. The paste-like dental glass composition according to claim 1, wherein the organic solvent (B) has a boiling point of 100 to 350° C.

6. The paste-like dental glass composition according to claim 1, wherein the organic solvent (B) has a viscosity at 20° C. of 20 mPa·s or more.

7. The paste-like dental glass composition according to claim 1, wherein the glass powder (A) has a glass transition temperature of 400 to 600° C.

8. The paste-like dental glass composition according to claim 1, wherein the glass powder (A) has a softening point of 500 to 680° C.

9. A method for producing a dental prosthesis, comprising firing the paste-like dental glass composition of claim 1 at 700 to 1,050° C.

10. A method for producing the paste-like dental glass composition of claim 1, which comprises mixing a glass powder (A), and an organic solvent (B) that is a dihydric alcohol compound having a C4 to C20 branched chain and that has a viscosity at 20° C. of 2,500 mPa·s or less.

11. The paste-like dental glass composition according to claim 1, wherein the paste-like dental glass composition has a paste runniness of 10 mm or less.

12. The paste-like dental glass composition according to claim 1, wherein the paste-like dental glass composition has a paste runniness of 5 mm or less.

13. The paste-like dental glass composition according to claim 1, wherein the paste-like dental glass composition has a paste runniness of 0.5 mm to 3 mm.

* * * * *